United States Patent [19]

Starks

[11] 4,105,699

[45] Aug. 8, 1978

[54] PREPARATION OF O-BENZYLPHENOL

[75] Inventor: Charles M. Starks, Ponca City, Okla.

[73] Assignee: Continental Oil Company, Ponca City, Okla.

[21] Appl. No.: 769,083

[22] Filed: Feb. 16, 1977

[51] Int. Cl.$^2$ ............................................. C07C 39/17
[52] U.S. Cl. ................................................... 568/744
[58] Field of Search ................................... 260/619 R

[56] References Cited

U.S. PATENT DOCUMENTS

| | | | |
|---|---|---|---|
| 2,140,782 | 12/1938 | Arnold et al. | 260/619 R |
| 2,678,951 | 5/1954 | Smith et al. | 260/619 R |
| 3,290,389 | 12/1966 | Hahn | 260/619 R |

Primary Examiner—Joseph E. Evans
Attorney, Agent, or Firm—Bayless E. Rutherford, Jr.

[57] ABSTRACT

A process for preparing o-benzylphenol in high selectivity is disclosed. The process comprises heating a mixture of benzyl alcohol and phenol in the presence of an effective amount of activated alumina as a catalyst.

9 Claims, No Drawings

PREPARATION OF O-BENZYLPHENOL

GENERAL BACKGROUND o-Benzylphenol is useful as a dye leveling agent for polyester fibers. Usually, it is made by treatment of phenol with benzyl chloride or benzyl alcohol in the presence of a strong acid such as aluminum chloride, zinc chloride or sulfuric acid. Unfortunately, this method produces a substantial amount of p-benzylphenol. In addition, the method presents corrosion problems and difficult operating techniques.

It is thus apparent that it would be desirable to have a process which prepares substantially pure o-benzylphenol (that is no para or meta isomers in the product). Our invention is directed to providing such a process.

PRIOR ART

A search of the prior art did not produce any reference teaching the specific process of our invention.

BRIEF SUMMARY OF THE INVENTION

Briefly stated, the present invention is directed to a process of preparing o-benzylphenol by contacting an admixture of phenol and benzyl alcohol at an elevated temperature and in the liquid phase with an effective amount of activated alumina catalyst.

Stated differently, the present invention is directed to an improvement in the preparation of o-benzylphenol by the reaction of phenol and benzyl alcohol wherein the improvement comprises contacting an admixture of phenol and benzyl alcohol at an elevated temperature in the liquid phase with an effective amount of activated alumina catalyst.

DETAILED DESCRIPTION

A suitable amount of phenol and benzyl alcohol is in the range of about 0.1 to 5 parts by weight of phenol to alcohol. On the same basis the preferred amount is in the range of about 1 to about 3.

Any activated alumina is suitable for use in our process.

A preferred activated alumina for use in our process is one prepared by the hydrolysis of aluminum alkoxides. The preferred activated alumina has the following properties:

Crystal Structure: α-alumina monohydrate
Surface Area, meters/gram: 230 – 300
$Al_2O_3$, weight percent *: 70 – 75
Loose bulk density, grams/liter: 650 – 720

* substantially all of the remainder is water.

A particularly suitable activated alumina is available from Conoco Chemicals Division of Continental Oil Company under the trademark "CATAPAL" ®SB.

A suitable amount of catalyst is in the range of about 1 to about 100 parts by weight of the combined amount of phenol and benzyl alcohol. On the same basis the preferred amount of catalyst is about 5 to about 35 parts by weight.

A suitable temperature range for conducting my process is in the range of about 125° to about 300° C. Preferably, the temperature is in the range of about 170° to about 200° C.

The process is conducted in the liquid phase since such a condition results in a product which is entirely o-benzylphenol. Conducting the process in the vapor phase results in the presence of some m-benzylphenol and p-benzylphenol in the product. In the present case this is considered undesirable.

Conducting the process in liquid phase may require application of some pressure to keep the reactants in the liquid state. It should be noted that at some temperatures no pressure is required. In any case, the pressure in the process will be in the range of 0 to 70 atmospheres.

The reaction time is in the range of about 0.1 to about 10 hours.

The desired o-benzylphenol product can be recovered from the organic product composition of the reaction by means of fractional distillation.

In the description provided herein we have stated both suitable ranges but that better results can be obtained using the preferred ranges.

In order to illustrate the nature of the present invention still more clearly the following examples will be given. It is to be understood, however, that the invention is not to be limited to the specific conditions or details set forth in these examples except insofar as such limitations are specified in the appended claims.

EXAMPLE 1

This example illustrates the process of my invention using powdered activated alumina. A mixture of 94 g (1.0 mole) of phenol, 65 g (0.6 mole) of benzyl alcohol and 15 g of calcined CATAPAL ®SB alumina powder was heated to reflux (185°–190° C) with an attached Dean-Stark trap containing 35 ml of toluene. After 1 hour the theoretical amount (10 ml) of water had been collected, and no further water was produced. After separation of the product by filtration, it was analyzed by gas chromatography and found to contain 4.4% toluene, 28.3% phenol, 0.65% benzylphenyl ether, 55% o-benzylphenol, and 11.7% higher boiling components (primarily, 5.1%, 2,6-benzylphenol). No m,p-benzylphenol was present in the product.

EXAMPLE 2

This example illustrates the process of my invention using pelleted activated alumina. The example also shows that the catalyst maintains its activity over a series of runs. Four runs were made in this example.

Run A

A mixture of 564 g (6.0 moles) of phenol, 324 g (3.0 moles) of benzyl alcohol and 89 g of pelleted and calcined CATAPAL SB alumina, mixed with 50 ml of toluene, was charged to a 2, 1 3-necked flask fitted with a thermometer, mechanical stirrer, and Dean-Stark trap with condenser. The reaction mixture was heated to reflux (N18° C) with very slow stirring (just enough to agitate the liquid without moving the catalyst pellets). The amount of water collected in the trap was measured as a function of time as an indication of the reaction rate. After no more water was produced the reaction mixture was cooled, and the liquid product poured off the catalyst. The total reaction time was 6¾ hours.

Runs B, C and D

The above-described procedure was repeated identically three more times using the same batch of catalyst. A plot of water produced vs time was made for each run. The plot for runs A, B, C and D were practically identical, thereby indicating that little, if any catalyst deactivation occurred during the four runs. Visual examination of the catalyst after the final run indicated no physical damage to the catalyst. The data for the feed composition, product, and organic product composition are summarized in Table I.

TABLE I

| Run No. | A | B | C | D |
|---|---|---|---|---|
| Feed Composition (wt., grams) | | | | |
| Benzyl Alcohol | 324.0 | 324.0 | 324.0 | 324.0 |
| Phenol | 564.0 | 564.0 | 564.0 | 564.0 |
| Toluene | 42. | 42. | 42. | 42. |
| Product Weight (grams) | | | | |
| Organic Product | 825.9 | 868.9 | 877.2 | 863.7 |
| Water Product | 62.4 | 46.5 | 55.7 | 56.0 |
| Loss by Adsorption on Catalyst | 41.7 | 14.6 | −2.9 | −6.3 |
| Organic Product Composition, % | | | | |
| Toluene | 5.95 | 5.82 | 6.10 | 6.29 |
| Phenol | 36.55 | 37.69 | 37.96 | 38.27 |
| Benzyl phenyl ether | 2.63 | 2.42 | 3.37 | 4.00 |
| Unknown | 0.59 | 0.51 | 0.61 | 0.60 |
| o-Benzylphenol* | 49.98 | 49.89 | 48.30 | 48.56 |
| High Boiling Components | 4.30 | 3.67 | 3.65 | 2.29 |

*No m,p-benzylphenol was observed in the product.

Thus, having described the invention in detail, it will be understood by those skilled in the art that certain variations and modifications may be made without departing from the spirit and scope of the invention as defined herein and in the appended claims.

I claim:

1. An improved process of preparing o-benzylphenol by the reaction of phenol and benzyl alcohol wherein the improved process comprises contacting an admixture of phenol and benzyl alcohol at a temperature in the range of about 125° to about 300° C. in the liquid phase in the presence of an effective amount of activated alumina, which is α-alumina monohydrate, catalyst.

2. The improved process of claim 1 wherein the phenol and benzyl alcohol are present in the range of about 0.1 to about 5 parts by weight of phenol to alcohol.

3. The improved process of claim 2 wherein the amount of activated alumina catalyst is in the range of about 1 to about 100 parts by weight of the combined amount of phenol and benzyl alcohol.

4. The improved process of claim 3 wherein the reaction time is in the range of about 0.1 to about 10 hours.

5. The improved process of claim 4 wherein the temperature is in the range of about 170° to about 200° C.

6. The improved process of claim 5 wherein the phenol and benzyl alcohol are present in the range of about 1 to about 3 parts by weight of phenol to alcohol.

7. The improved process of claim 6 wherein the amount of activated alumina catalyst is in the range of about 5 to about 35 parts by weight of the combined amount of phenol and benzyl alcohol.

8. The improved process of claim 7 wherein the reaction product contains no m-benzylphenol and no p-benzylphenol.

9. The process of claim 8 wherein the activated alumina has the following additional properties:

surface area, meters/gram: 230 – 300

$Al_2O_3$, weight percent: 70 – 75 loose bulk density, grams/liter: 650 – 720.

* * * * *

UNITED STATES PATENT OFFICE
CERTIFICATE OF CORRECTION

PATENT NO. : 4,105,699
DATED : August 8, 1978
INVENTOR(S) : Charles M. Starks

It is certified that error appears in the above-identified patent and that said Letters Patent are hereby corrected as shown below:

Column 2, line 14, after "suitable" the following was omitted, "and preferred ranges. It is to be understood that the process is operable using the suitable".

Column 2, line 49, "2, 1 3-necked" should be --2 1, 3-necked--.

Column 2, line 52, "(N18°C)" should be --(∼180°C)--.

Signed and Sealed this

Sixteenth Day of January 1979

[SEAL]

Attest:

RUTH C. MASON
Attesting Officer

DONALD W. BANNER
Commissioner of Patents and Trademarks